(12) United States Patent
Hodjat et al.

(10) Patent No.: US 10,839,938 B2
(45) Date of Patent: Nov. 17, 2020

(54) FILTERING OF GENETIC MATERIAL IN INCREMENTAL FITNESS EVOLUTIONARY ALGORITHMS BASED ON THRESHOLDS

(71) Applicant: Cognizant Technology Solutions U.S. Corporation, College Station, TX (US)

(72) Inventors: Babak Hodjat, Dublin, CA (US); Hormoz Shahrzad, Dublin, CA (US)

(73) Assignee: Cognizant Technology Solutions U.S. Corporation, College Station, TX (US)

( * ) Notice: Subject to any disclaimer, the term of this patent is extended or adjusted under 35 U.S.C. 154(b) by 470 days.

(21) Appl. No.: 15/791,277

(22) Filed: Oct. 23, 2017

(65) Prior Publication Data

US 2018/0113977 A1  Apr. 26, 2018

Related U.S. Application Data

(60) Provisional application No. 62/413,324, filed on Oct. 26, 2016.

(51) Int. Cl.

| G01N 33/48 | (2006.01) |
|---|---|
| G01N 33/50 | (2006.01) |
| G16B 20/00 | (2019.01) |
| G06F 19/00 | (2018.01) |
| G16B 40/00 | (2019.01) |
| G16H 50/70 | (2018.01) |

(52) U.S. Cl.
CPC ........... *G16B 20/00* (2019.02); *G06F 19/321* (2013.01); *G16B 40/00* (2019.02); *G16H 50/70* (2018.01)

(58) Field of Classification Search
None
See application file for complete search history.

(56) References Cited

U.S. PATENT DOCUMENTS

| 8,527,433 B2 | 9/2013 | Hodjat et al. |
| 8,768,811 B2 | 7/2014 | Hodjat et al. |
| 9,466,023 B1 | 10/2016 | Shahrzad et al. |
| 2009/0125370 A1 | 5/2009 | Blondeau et al. |

FOREIGN PATENT DOCUMENTS

WO   WO-2016057521 A1 *  4/2016  ......... G06K 9/00342

OTHER PUBLICATIONS

Koza, "Genetic Programming: On the Programming of Computers by Means of Natural Selection", Dec. 1992, MIT Press, pp. 1-609.

* cited by examiner

*Primary Examiner* — Russell S Negin
(74) *Attorney, Agent, or Firm* — Dawn-Marie Bey; Bey & Cotropia PLLC

(57) ABSTRACT

Roughly described, a computer-implemented evolutionary data mining system implements a genetic algorithm. The Genetic algorithm includes a requirements checkpoint, which selects individuals for discarding from the pool of candidate genomes which do not meet a predetermined minimum behavioral requirement for operating in production. The requirements checkpoint enforces an absolute minimum threshold for a behavioral characteristic of the individual, and is different from a competition step in which individuals are selected for removal on the basis of comparisons with each other. A requirements checkpoint may be inserted at various points within the genetic algorithm flow or at reasonable intervals during the training cycle. If at any of these checkpoints the minimum requirement is not met, the candidate individual may be removed from the candidate pool.

24 Claims, 4 Drawing Sheets

FILTERING OF GENETIC MATERIAL IN INCREMENTAL FITNESS EVOLUTIONARY ALGORITHMS BASED ON THRESHOLDS

CROSS-REFERENCE TO OTHER APPLICATIONS

This application claims priority to U.S. Provisional Application No. 62/413,324, filed Oct. 26, 2016, entitled "FILTERING OF GENETIC MATERIAL IN INCREMENTAL FITNESS EVOLUTIONARY ALGORITHMS BASED ON THRESHOLDS", which is incorporated by reference herein.

BACKGROUND

The invention relates generally to data mining, and more particularly, to the use of genetic algorithms to extract useful rules or relationships from a data set for use in controlling systems.

In many environments, a large amount of data can be or has been collected, which records experience over time within the environment. For example, a healthcare environment may record clinical data, diagnoses and treatment regimens for a large number of patients, as well as outcomes. A business environment may record customer information such as who they are, what they do, and their browsing and purchasing histories. A computer security environment may record a large number of software code examples that have been found to be malicious. A financial asset trading environment may record historical price trends and related statistics about numerous financial assets (e.g., securities, indices, currencies) over a long period of time. Despite the large quantities of such data, or perhaps because of it, deriving useful knowledge from such data stores can be a daunting task.

The process of extracting patterns from such data sets is known as data mining. Many techniques have been applied to the problem, but the present discussion concerns a class of techniques known as genetic algorithms. Genetic algorithms have been applied to all of the above-mentioned environments.

Evolutionary algorithms, which are a superset of genetic algorithms, are good at traversing chaotic search spaces. See, for example, Koza, J. R., "Genetic Programming: On the Programming of Computers by Means of Natural Selection", MIT Press (1992), incorporated by reference herein. The basic elements of an evolutionary algorithm are an environment, a model for a genotype (usually referred to herein as an "individual"), a fitness function, and a procreation function. An environment may be a model of any problem statement. An individual may be defined by a set of rules governing its behavior within the environment. A rule may be a list of conditions in conjunction with an action that the rule asserts should be performed in the environment. A fitness function is used for evaluating the fitness of each individual in the environment, and fitness may be defined by the degree to which an evolving rule set is successfully negotiating the environment. A procreation function generates new individuals by mixing genetic material (e.g., rules or sets of rule conditions) from parents selected from among the fittest individuals. Thus, a new individual is different from either parent, though it retains some of each parents' genetic material. In each generation, a new population of individuals is created.

A genetic algorithm attempts to find an optimum solution, as defined by the fitness function, to the target problem. It uses techniques that attempt to emulate Darwinian evolution. At the start of the evolutionary process, an initial population of individuals is created randomly by putting together the building blocks, or alphabets, that form an individual. Once a population is established, individuals are tested against sample input data, and their performance on the sample input data is evaluated using the fitness function. The fitness function assigns a score which is an estimate of the individual's contribution to the problem solution. Individuals with the best fitness estimate are then used to create the next generation. Through procreation, rules of parent individuals are mixed, and sometimes mutated (i.e., a random change is made in a rule) to create a new rule set. This new rule set is then assigned to a child individual that will be a member of the new generation. In some incarnations, known as elitist methods, the fittest members of the previous generation, called elitists, are also preserved into the next generation.

When a candidate individual is first created, it may do a bad job at solving the problem and hence have a low fitness. But the genetic algorithm evolves the pool incrementally by discarding the least fit individuals, using the most fit individuals as parents in the procreation step to generate new individuals by crossover and/or mutation, and repeating the evaluation of the new pool of candidate individuals. The expectation is that after a large number of generations of this evolutionary process, the fittest individuals then in the pool will embody the optimal solutions to the target problem.

SUMMARY

A fitness function produces the fitness estimate for an individual based on the individual's performance in response to a set of input data. Various characteristics of an individual's performance in response to training samples may be scored and weighted in the fitness function. The fitness function aggregates the weighted scores. However, with multiple desirable characteristics being used to evaluate the fitness of an individual, the fitness estimate alone may not be sufficient to ensure that an individual meets certain absolute requirements of the solution. For example, a fitness function may optimize for the solution having the best results, but may not take into account the time that the individual requires to achieve those results. Time (or some other behavioral characteristic) may be an absolute minimum requirement of any individual that is to be put into production for solving the target problem. Furthermore, while it may be possible to include time in the factors considered by the fitness function, the genetic algorithm does not treat any of its input factors as an absolute. Thus the fitness function itself does not guarantee than the individual netting the most money from task scheduling will complete the task before a required deadline.

To address this issue, roughly described, embodiments of the present invention insert a separate requirements checkpoint into the process that tests that an individual meets minimum absolute requirements for some behavioral characteristic. Individuals that do not meet minimum requirements may be removed from the system. Whereas the fitness estimate score is used to determine a relative fitness ranking among individual candidates, the requirements evaluation determines whether a single individual meets a minimum requirement (which may be a fixed threshold) for operating in production.

Roughly described, a computer-implemented evolutionary data mining system includes a memory storing a database having a candidate pool comprising a set of candidate individuals, each candidate individual identifying a plurality of conditions and at least one corresponding consequence to be asserted in dependence upon the conditions, each candidate individual further having associated therewith a respective testing experience level and a respective fitness estimate. The system performs at least the following steps: candidate testing, fitness updating, requirements checking, competition, and procreation. In the candidate testing step, individuals from the candidate pool are tested on the training data, which increases the individual's testing experience level. the fitness update step updates the fitness estimate associated with each of the individuals in dependence upon both the training data and the outputs proposed by the respective individual in the testing. The requirements checking step (at a "requirements checkpoint") selects individuals for discarding from the candidate pool which do not meet a predetermined minimum behavioral requirement for operating in production. The competition step selects individuals for discarding from the candidate pool in dependence upon their updated fitness estimates, and the procreation step forms new individuals in dependence upon a respective set of at least one parent individual from the candidate pool.

The requirements checkpoint may be inserted at various points within the flow or at reasonable intervals during the training cycle. If at any of these checkpoints the minimum requirement is not met, the candidate individual may be removed from the candidate pool.

The above summary of the invention provides a basic understanding of some aspects of the invention. This summary is not intended to be precise, nor to identify key or critical elements of the invention or to delineate the scope of the invention. Its sole purpose is to present some concepts of the invention in a simplified form as a prelude to the more detailed description that is presented later. Particular aspects of the invention are described in the claims, specification and drawings.

BRIEF DESCRIPTION OF THE DRAWINGS

The invention will be described with respect to specific embodiments thereof, and reference will be made to the drawings, in which.

DETAILED DESCRIPTION

Figure 1:
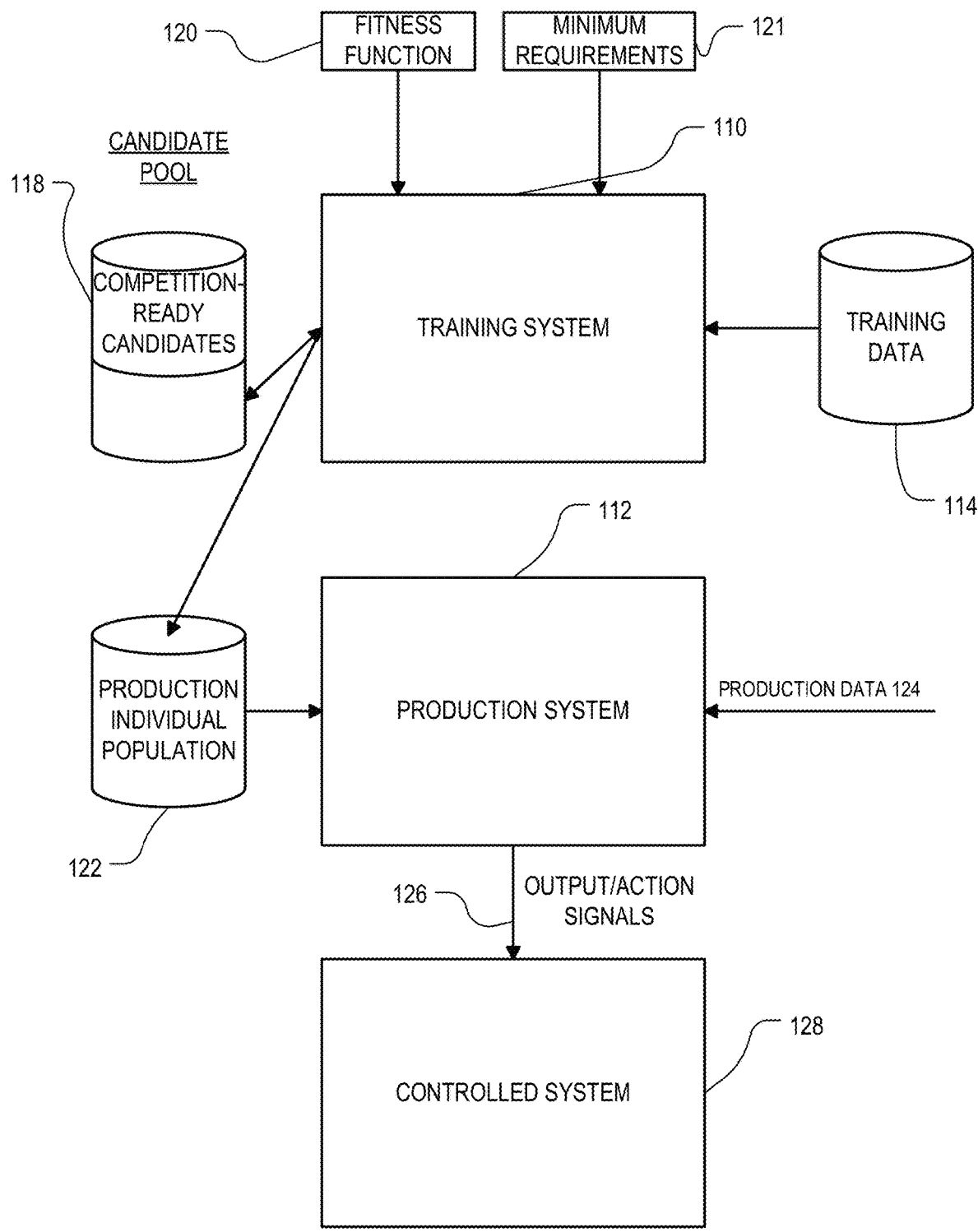
FIG. 1 is an overall diagram of an embodiment of a data mining system incorporating features of the invention.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Data mining involves searching for patterns in a database. Individuals are evolved and tested against training data and selected based on some measure of success when processing the training data. In embodiments herein, the database is a training database, and the result is also represented in some way in the database. The fittest individuals are considered to be those that assert actions that optimize for some result.

Each individual includes an identifier, an indication of the amount of testing it has undergone, and the individual's current fitness estimate based on its performance on the testing data. An individual also includes one or more "rules", each of which contains one or more conditions and an output to be asserted if all the conditions in a given input data sample are true. During procreation, a new individual may inherit any of the conditions or outputs, any of which may be altered (mutated).

For some applications, an individual may be associated with a stateful object, and the actions asserted by the rules of an individual may change the state of the associated object. (Examples are provided below). A fitness function may determine fitness based on comparing the accuracy of an individual's asserted actions on a single sample, or may examine the state of the associated object after more than one data sample is processed, and potentially more than one action is asserted. The individual's fitness level may be determined by averaging (or otherwise combining) scores over the all the trials.

Mature and fit individuals are selected to identify patterns in production data which are likely to produce the desired result.

Example Application Domains

There are many examples of application domains that can benefit from data mining. Each has a way of using a genetic algorithm and the techniques described herein to derive a solution. In this section, some of the application domains are described. These application domains are referred to throughout this document.

Health Care

In a healthcare environment, an individual can be used to point out patterns in diagnosis and treatment data which should be studied more closely as likely either improving or degrading a patient's diagnosis. An individual can be thought of as a set of rules predicting a patient's future state, given the patient's current and past state. An individual in a health care application may be trained on data collected for patients having certain symptoms, medical history, and the established diagnosis. The output of the rules can be proposed diagnoses or proposed treatment regimens that the individual asserts are appropriate given the conditions of the individual's rules. The indicators on which the rules are based can be a patient's vital signs, and past treatment and medication history, for example. An example rule is as follows:

if pulse>=120 and 18<=blood pressure[6]<20 and temp>=104 and surgery duration<22 and clamp on artery and medication=EB45 and last medication>=60 and !white blood cell count [3]<−2.3 and !oxygen level [1]<−1.1-->>> then thromboembolism @ prob<=0.65

In the healthcare domain, an individual (genome) might propose a diagnosis based on patient prior treatment and current vital signs, and fitness may be measured by the accuracy of that diagnosis as represented in the training data. The fitness of a healthcare genome may be determined by aggregating how close the individual predicts the established outcome across a large number of data samples.

Financial Trading

In a financial assets trading environment, the individual can be used to detect patterns in real time data and assert trading signals to a trading desk. An individual can be thought of as a virtual trader that is given a hypothetical sum of money to trade using historical data. The fitness of an individual may be evaluated based on the monetary value (i.e. final state) of a stateful object (i.e., securities holding) after processing historical market data. An individual trader performs trades in accordance with a set of rules that define the individual thereby prompting it to buy, sell, hold its position, or exit its position. Rules may also be designed to contain gain-goal and stop-loss targets, thus rendering the exit action redundant. A hold occurs when no rule in the individual is triggered; therefore, the individual effectively holds its current position.

Training data for a financial assets trading environment may include a security name and price. Each sample of training data may include a historical date, an identification of a particular security or other financial asset (such as a particular stock symbol), and raw historical market data for that financial asset over a particular time interval (for example, one entire day). The indicators on which the rules are based can be, for example, a time increment ("tick"), or the closing price for a stock day.

The following code defines an example rule in terms of conditions and indicators, as well as the action asserted by the rule, in accordance with one embodiment of the present invention:

if (PositionProfit>=2% and !(tick=(-54/10000)% prev
       tick and MACD is negative)
    and !(tick=(-119/10000)% prev tick and Position is long))
    and !(ADX×100<=5052))
    then SELL where "and" represents logical "AND" operation, "!" represents logical "NOT" operation, "tick", "MACD" and "ADX" are stock indicators, "SELL" represents action to sell, and "PositionProfit" represents the profit position of the individual.

The goal is to maximize the value of a securities holding after responding to price fluctuations of the security over some period of time, for example, over a day. An individual's fitness may be measured by the individual's ability to make a profit, or the ability to do so while maintaining stability, or some other desired property. Each individual has associated with it a state of the account it is managing. The value of that account after carrying out the actions recommended by the individual may be compared to the value of other individual's accounts after processing the same training data to determine which individual is relatively more fit.

Scheduling Tasks/Resources

Another example is a system in which individuals are trained to assign resources to tasks in which assigning a task to a set of resources costs money and task completion earns money. The goal is to make money while complying with constraints such as obeying local laws and regulations. Heterogeneous resources may have different characteristics to offer, and heterogeneous tasks require different sets of characteristics in a resource to complete the tasks. An example of this kind of application is a computer hosting service in which computing tasks are assigned to compute nodes. The requirements of the tasks such as amount of memory, disc space, execution environment, network connectivity, etc. must be provided by the assigned compute node. In addition, certain compute nodes have restrictions on tasks that may be assigned. For example, if the compute node is in a foreign country, there may be a restriction that the task cannot perform encryption.

The training data for such a task/resource scheduler may include the introduction of task requests including requirements, as well as the reconfiguration events that may add, remove, relocate, or change the capabilities of a compute node.

The fitness function may be configured to value certain qualities of the schedule more than others. For example, in addition to determining the dollar value to the hosting service of a scheduling assignment, other attributes that are not monetized may be factored into the fitness function such as minimizing the heat produced by computers in a single room.

Robotic Navigation

In many applications in which genetic algorithms are used, the fitness of an individual can be calculated exactly because each individual is evaluated on only a limited amount of data, and the data is the same for all the individuals. The individual can be tested on all samples of the training data, and its fitness can be calculated exactly.

For example, in a genetic algorithm designed for finding the best algorithm for a robot to use to traverse a room containing obstacles, the fitness of a particular traversal algorithm (i.e. the fitness of a particular solution, or "individual") can be calculated from the amount of time it takes the robot to reach the far wall of the room. The less time it takes, the greater the fitness of the traversal algorithm that was used. To evaluate fitness, the robot is placed into the room (physically or in a computer simulation), given the particular traversal algorithm to be tested, and started on its way.

If the goal is to find the best solution for traversing a particular room with a single arrangement of objects (i.e. a single sample of training data), then the testing of an individual can be completed with a single traversal of the room. In this case there is no uncertainty about an individual's fitness; it is an exact fitness value, not an estimate. The fitness values for various individuals then can be compared in a competition step, and the individuals with the best fitness value can be retained and used as parents in the reproduction step to generate new individuals to test.

Embodiments of the presents' invention, on the other hand, can operate in an environment in which there is a substantial amount of training data, so much, in fact, that it is impossible to test an individual on all of the available data samples. In the robot learning example above, this situation might correspond to one in which the goal is not to find an individual that optimizes traversal speed for a particular room with a single arrangement of objects, but to find an individual that optimizes traversal speed for arbitrary placement of the obstacles. That is, in the first example above the obstacles are always placed at fixed locations in the room, and the goal is to find an individual that navigates them best, whereas in the second example the goal is to find an individual that navigates obstacles best no matter where they are placed in the room.

In this second example, if an individual is tested on only a single arrangement of objects (i.e. one data sample), the robot's traversal speed across the room will provide only one estimate of the individual's fitness. And since an individual that does well in one room configuration might do poorly in another room configuration, and vice-versa, there is very little confidence that this one fitness value accurately indicates the true fitness for that solution. It would be better to test the individual over multiple possible room configurations (multiple data samples), and average or otherwise combine the results. This would provide a fitness value estimate which carries higher confidence that it accurately indicates the true fitness of that individual. However, it is still only an estimate. One would have to test each individual over all possible placements of the obstacles in order to be 100% confident that the fitness score is accurate. That amount of testing would be prohibitive or impossible, but it is clear that for this kind of problem, the more data samples (room configurations) that the individual is tested on, the greater the confidence is that the resulting fitness estimate accurately indicates the true fitness for that individual. Only then is the competition step likely to select individuals that really are fitter than the others.

Determining Fitness of Individuals

In an embodiment, a sample may comprise multiple sets of input indicators. An individual may produce an output recommendation for each set of input indicators (that is, each single data point in the data samples); however, there may be a single cumulative or aggregated output for the sample as a whole. For example, each output produced when applying each single data point may be scored, and the overall fitness score may be an aggregation of the scores for each single data point. Alternatively, each output may impact the state of an object, and the fitness determined based on the final state of the object after all the samples in a trial are applied.

The fitness estimate for an individual is likely to be inaccurate as testing begins, and confidence in its accuracy may increase as the individual is tested on more samples. This means that if an individual is "lucky" early on, in the sense that the first set of samples that it was given for testing happened to have been in some sense "easy", then after only the first set of samples the individual will appear to be fitter than it actually is. If compared to other individuals that have much more experience, lucky individuals could displace individuals whose fitness estimates are lower but more realistic. If care is not taken, therefore, the algorithm will optimize for individuals that are lucky early on, rather than their actual fitness.

A solution to this problem is to consider individuals for competition only after they have completed testing on a predetermined number of samples, for example 1000 samples. Once an individual has reached that minimum threshold experience level, comparisons with other individuals are considered valid and can compete on the basis of fitness against other competition-ready individuals.

Introducing Requirements Checkpoint

A benefit of having a fitness function to evaluate the performance of an individual is that the rules of the individual can take into account many different indicators. However, when the problem domain dictates that there are absolute minimum requirements that an individual must meet, the fitness function is not able to ensure that the most fit individuals will also meet the minimum requirements. For example, a fitness function may optimize for the solution having the best results, but may not take into account the time that the individual requires to achieve those results. Time (or some other behavioral characteristic) may be an absolute minimum requirement of any individual that is to be put into production for solving the target problem. Furthermore, while it may be possible to include time in the factors considered by the fitness function, the genetic algorithm does not treat any of its input factors as an absolute. Thus the fitness function itself does not guarantee than the individual netting the most money from task scheduling will complete the task before a required deadline. To address this issue, embodiments of the present invention insert a separate requirements checkpoint into the process that tests that an individual meets minimum absolute requirements for some behavioral criteria. Individuals that do not meet minimum requirements may be removed from the system. Such embodiments also may face a decision of when to discard an individual that does not meet a minimum requirement. There is a tradeoff between a) encouraging diversity among a population to avoid the algorithm converging to a local optimum without finding the global optimal solution and b) spending resources to train and compete individuals that are known to be deficient in some way, as well as to create, train, and compete individuals that are procreated from such a deficient individual in which the deficiency may be inherited by the children.

The choice of where to insert the requirements checkpoint depends on the application-specific tradeoff of considering filtering too soon versus too late. The ideally positioned checkpoint helps to guide the search for a solution into a particular area of the search space and away from other areas that are not likely to be fruitful. The fitness function performs the search in an area selected by the requirements checkpoint. The goal of removing such an individual before allowing it to pass its genetic material to a new individual is to discourage the creation of new individuals that do not meet the minimum requirements of a solution. In some embodiments a requirements checkpoint is not inserted until the system is selecting individuals for deployment into production.

The fitness function assigns an estimate based on the output of an individual over a set of training samples. Sometimes, a fitness function can reward individuals for not producing an output, or for producing an output that does not have an effect on the system. For example, an individual in a financial trading system may start the process with a security holding of a certain value. If the training data does not cause any of the rules to fire in an individual, the value of the holding would stay the same. Other individuals that produce an output in response to the training data may lose value in the security holding. Thus it can occur that the individual producing no output is be assigned a higher fitness estimate than an individual that asserted an output that caused an undesirable result. However, a test that does not cause an individual to output an action provides no insight into the behavior of the individual. Producing no output is qualitatively different than producing an output that maintains the current value of the security holdings. Individuals are sought having rules that both fire and produce a desirable output.

An embodiment of the invention may require the participation of an individual (that is, responding to input samples and producing an output) to the solution in order to remain in the pool. An individual's participation in the solution (referred to herein as activity characteristics) is not normally evaluated by the fitness function. However, an embodiment may require an individual to exhibit at least a minimum level of activity. Activity of an individual, as used herein, relates to the number of samples (or data points within samples) that activate the individual to assert one of a particular set of consequences or resulting in a particular set of outcomes. An active sample causes at least one of the rules in the individual to fire. An embodiment may prescribe a minimum activity level as a percentage of active samples to total samples tested. If an individual does not produce any output for some portion of the input data, then the individual has not been effectively tested because the sample data did not satisfy the indicator conditions of the rules in the ruleset.

A threshold may be established indicating a required minimum amount of activity that an individual must demonstrate. An embodiment may prescribe a minimum activity threshold as a statistically significant minimum rate for a candidate individual producing an output for input data. Using such activity thresholds as an absolute requirement ensures that only candidates that have a statistically significant rate of asserting consequences that affect the outcome are accepted. For example, if an individual has been tested on 50,000 samples and only asserted a consequence on less than 50 of them, the activity percentage is less than half a percent, which is likely lower than the activity threshold. Such an individual would not meet the minimum activity requirement in such an embodiment.

Another form of activity threshold might be calculated by grouping testing data samples and measuring activity per group. For example, a calendar-day activity threshold for a system in which the input data represents one day of trading may aggregate the activity over calendar days and ensure that the overall calendar-day activity meets a certain threshold. Activity thresholds can also be applied to the activity of each rule within an individual. Failure to meet the minimum activity requirement may cause the candidate to be removed from the candidate pool. In one embodiment, when the minimum activity level is applied to activity of particular rules within an individual, just the inactive rules may be removed from the individual and the rest of the individual's genetic material retained to create a new individual that is introduced as a new candidate with no experience (not tested on samples yet) back into the candidate pool to be tested again.

To determine activity percentages for one or more individuals, additional data is recorded at testing time. An individual activity level counter may be incremented for each testing sample during which the individual produced an output (i.e., one or more rules in the ruleset fired). For example, the testing process may record data for each sample including: a sample identifier, an individual identifier, one or more rule identifiers of rules that fired for this sample, and for each rule that fired, the corresponding output from the rule. This data may be aggregated in different ways such as: for each rule, the number or percentage of samples that caused it to fire; for each individual, the number or percentage of samples causing any one of its rules to fire. (As used herein, "number or percentage of samples" is sometimes referred to herein generically as a "portion" of samples.)

Requirements other than minimum activity levels may be tested at a checkpoint. In other embodiments, the requirement may involve a minimum return on investment or a percentage of time a particular output was issued. For example, in a system evolving trading strategies a threshold may be defined for the total return over a number of trading days divided by the total money traded during that time. Another example is that thresholds may be established for a minimum number of long and short positions to be taken over time for an evolved trading strategy.

The previous examples showed minimum requirements based on the asserted recommendation. A more complicated requirement may be based on the effect that an asserted recommendation has on the state of an object associated with the individual. For example, a securities trading individual may assert instructions to place a limit order. However, when the limit order may not fill. When the limit order does not fill, the position of the security is not affected. Again, an individual that asserts limit orders that too often do not fill, may be considered by the target problem as lacking sufficient activity for use in the production system and may be checked for at a requirements checkpoint.

The minimum requirements checked for in various embodiments typically are absolutes, in the sense that they do not dependent on the fitness of the individual. Checking for the minimum requirements does not involve a comparison with other individuals. The minimum requirements also typically are requirements of behavior of an individual. As used herein, the "behavior" of an individual is the manner in which the individual conducts itself when faced with stimuli, such as a data sample in training or a data sample in production. The behavior of an individual is not easily predicted from the rule set itself especially where the rationales for the rules are unobvious, as is typically the case for a machine-learned rule set. The behavior of an individual is not easily predicted also because typically it depends on the data samples that the individual faces in operation. Behavior of an individual is different from the contents of the individual itself fitness, and different from the individual's fitness level. It is something that is determined by observing the individual in operation. Activity, for example, is part of the behavior of an individual. In embodiments herein, requirements checkpoints set thresholds for minimum behavioral requirements that an individual must satisfy in order to be accepted for use in production. Typically the minimum behavioral requirements are determined in advance and fixed for a particular target problem, and do not change with each batch of training data, or each battery of tests, or in dependence upon the fitness estimate of any individual in the candidate pool.

A requirements checkpoint may be inserted into the training process before one or more operations in the flow. The position of the checkpoint within the flow depends on the nature of the test performed at the checkpoint and how individuals that fail the test are to be treated during training. Multiple checkpoints may be introduced, each potentially testing for compliance with a different requirement. For example, in an embodiment, a requirements checkpoint that tests an individual against one or more activity thresholds may be performed at maturity. Maturity, as the term is used herein, is defined as the earliest time an individual is permitted to participate in competition and/or procreation. Performing the checkpoint at maturity removes inactive individuals from the system after the individual has been tested enough to have had the opportunity to demonstrate sufficient activity and before the individual can pass its characteristics (that is, genetic material) to new individuals. The reason to insert a requirements checkpoint no later than when it reaches maturity is to prevent an individual that does not meet minimum requirements from propagating undesirable characteristics to new individuals. The reason to insert the requirements checkpoint no earlier than when it reaches maturity is to ensure that the individual has been tested on a sufficient number of samples to be relatively certain that its demonstrated activity level will be its norm.

An example of using an activity threshold in a requirements checkpoint is selecting individual rulesets for classifying blood pressure. The system can detect state transitions of low to normal, normal to high, high to normal, normal to low, and normal to normal. Even though most samples may be classified as normal to normal, for some minimum number or percent of samples, the training system needs to ensure that rules are available that output the other transitions as well. A requirements checkpoint could select for individuals that output a transition other than normal to normal. Rulesets that have not fired at all or only output normal to normal transitions may be discarded.

Example Embodiment

FIG. 1 is an overall diagram of an embodiment of a data mining system incorporating features of the invention. The system is divided into three portions, a training system 110, a production system 112, and a controlled system 128. The training system 110 interacts with a database 114 containing training data, as well as with another database 116 containing the candidate pool. As used herein, the term "database" does not necessarily imply any unity of structure. For example, two or more separate databases, when considered together, still constitute a "database" as that term is used herein. The candidate pool database 116 includes a portion 118 containing the individuals that are competition-ready. The training system 110 operates according to a fitness function 120, which indicates to the training system 110 how to measure the fitness of an individual. The training system 110 optimizes for individuals that have the greatest fitness, according to the fitness function 120. The fitness function is specific to the environment and goals of the particular application. For example, the fitness function may be a function of the predictive value of the individual as assessed against the training data—the more often the individual correctly predicts the result represented in the training data, the more fit the individual is considered. One or more sets of minimum requirements 121 are thresholds that may be used for a requirements checkpoint.

In one embodiment, the training system may be implemented by one evolutionary engine (EE) running on a computer system. The evolutionary engine creates, tests, and harvests the best individuals to be used in production system 112. In another embodiment, more than one EE may create and test individuals, and individuals may be passed from one EE to another for further testing. In another embodiment, an evolutionary coordinator (EC) may receive individuals from one or more EEs and have the individuals from different engines compete among themselves. An EC may select the best individuals across multiple EEs and cause these selected individuals to be deployed in the production system 112. There may also be a hierarchy of ECs, with EE's at the leaf nodes of the hierarchy, such as described in U.S. Pat. No. 9,466,023, entitled Data Mining Technique With Federated Evolutionary Coordination, incorporated herein by reference.

The training data is arranged in the database 114 as a set of samples, each with parameters and their values, as well as sufficient information to determine a result that can be compared with an assertion made by an individual on the values in the sample. In one embodiment, the result is explicit, for example, a number set out explicitly in association with the sample. In such an embodiment, the fitness function can depend upon the number of samples for which the individual's output matches the result of the sample. In another embodiment, such as in the financial asset trading embodiment, the result may be only implicit.

In one embodiment, the individuals in candidate pool 116 are stored and managed by conventional database management systems (DBMS), and are accessed using SQL statements. Thus a conventional SQL query can be used to obtain, for example, all individuals having a minimum fitness level. New individuals can be inserted into the candidate pool 116 using the SQL "insert" statement, and individuals being discarded can be deleted using the SQL "delete" statement. In another embodiment, the individuals in candidate pool 116 may be stored in a linked list. In such an embodiment insertion of a new individual can be accomplished by writing its contents into an element in a free list, and then linking the element into the main linked list. Discarding of individuals involves unlinking them from the main linked list and re-linking them into the free list.

Note that in some embodiments individuals selected for discarding are not always immediately discarded; they are marked in some way has having been selected for discarding, but may actually be retained for historical or other reasons. But they no longer participate fully in the evolutionary process. For example, they might no longer undergo further testing, might not be included in competition among individuals, and/or might not be involved in further procreation. As described elsewhere herein, an individual selected for discarding for failure to satisfy minimum requirements for use in production does not participate fully in future procreation, though in some embodiments some of its genetic material might still be used.

The production system 112 operates according to a production individual population in another database 122. The production system 112 inputs production data 124 to these individuals, and produces outputs 126, which may be action signals or recommendations. In the financial asset trading environment, for example, the production data 124 may be a stream of real time stock prices and the outputs 126 of the production system 112 may be the trading signals or instructions that one or more of the individuals in production individual population 122 outputs in response to the production data 124. In the healthcare domain, the production data 124 may be current patient data, and the outputs 126 of the production system 112 may be a suggested diagnosis or treatment regimen that one or more of the individuals in production individual population 122 outputs in response to the production data 124. The production individual population 122 may be harvested from the training system 110 once or at intervals, depending on the embodiment. Preferably, only competition-ready individuals 118 are permitted to be harvested. In an embodiment, further selection criteria is applied in the harvesting process.

The controlled system 128 is a system that is controlled automatically by the signals 126 from the production system. In the financial asset trading environment, for example, the controlled system may be a fully automated brokerage system which receives the trading signals via a computer network (not shown) and takes the indicated action. Depending on the application environment, the controlled system 128 may also include mechanical systems such as engines, air-conditioners, refrigerators, electric motors, robots, milling equipment, construction equipment, or a manufacturing plant.

Figure 2:
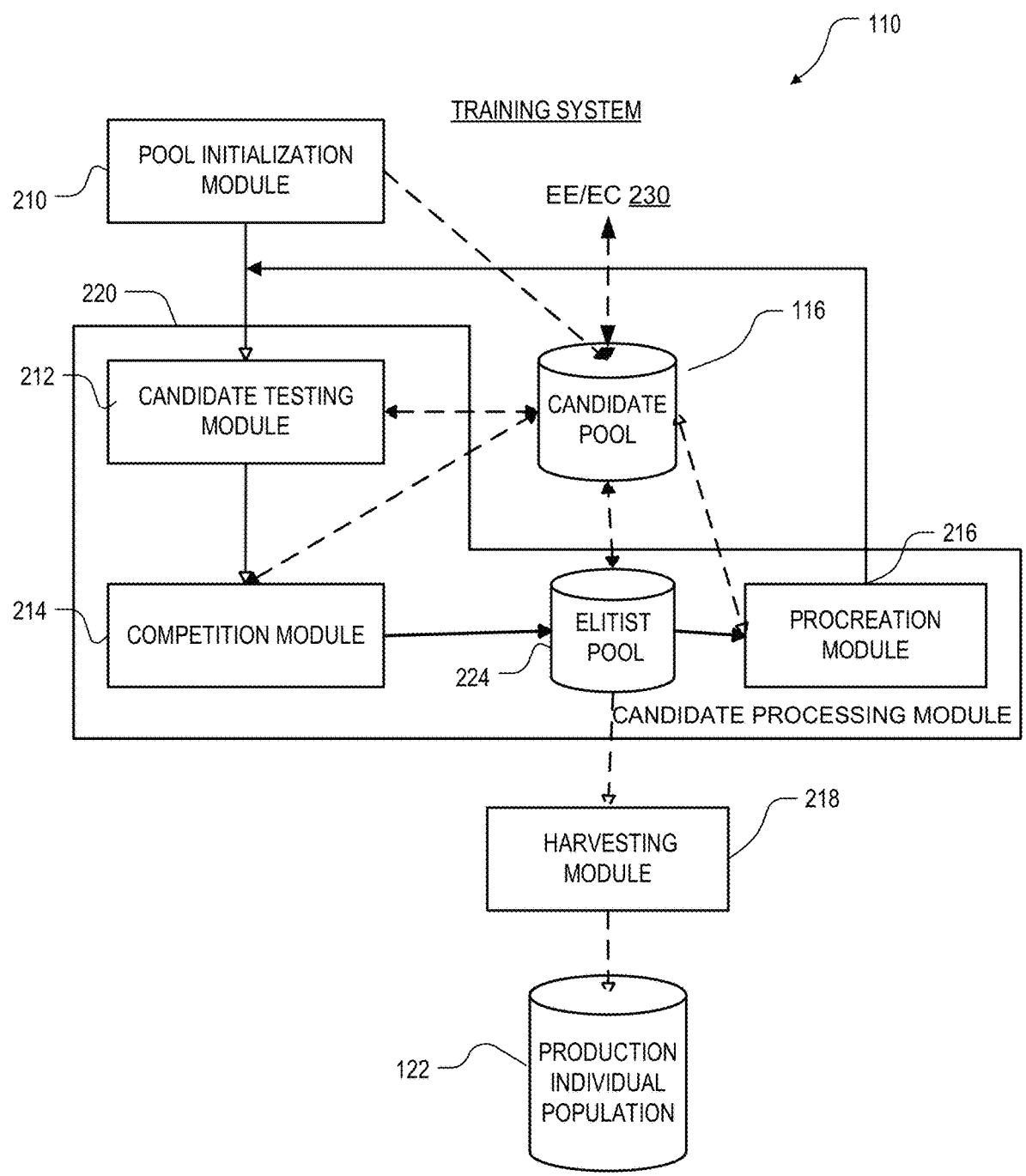
FIG. 2 illustrates modules that can be used to implement the functionality of the training system in FIG. 1, according to an embodiment of the invention.

FIG. 2 illustrates various modules that can be used to implement the functionality of training system 110 (FIG. 1). Candidate pool 116 and production individual population database 122 are also shown in the drawing. Solid lines indicate process flow, and broken lines indicate data flow. The modules can be implemented in hardware or software, and need not be divided up in precisely the same blocks as shown in FIG. 2. Some can also be implemented on different processors or computers, or spread among a number of different processors or computers. In addition, it will be appreciated that some of the modules can be combined, operated in parallel or in a different sequence than that shown in FIG. 2 without affecting the functions achieved. Also as used herein, the term "module" can include "sub-modules", which themselves can be considered herein to constitute modules. In particular, the candidate testing module 212, competition module 214, and procreation module 216 are also considered herein to be sub-modules of a candidate processing module 220. The blocks in FIG. 2 designated as modules can also be thought of as flowchart steps in a method.

Referring to FIG. 2, the candidate pool 116 is initialized by pool initialization module 210, which creates an initial set of candidate individuals. These individuals can be created randomly, or in some embodiments a priori knowledge may be used to seed the first generation. At the start, all new individuals are initialized with no experience/maturity and a fitness estimate that is undefined. In another embodiment, the candidate pool may also include individuals remaining in an elitist pool 224 from a previous generation. In addition, individuals may be received from an external EC 230 and added to the candidate pool to undergo further testing. Candidate testing module 212 then proceeds to test the population in the candidate pool 116 on the training data 114. Each individual undergoes a battery of tests or trials on the training data 114. A battery of tests may include, for example, on the order of 1000 trials. In one embodiment, the battery of tests includes at least the minimum number of trials for each individual to qualify for competition with other individuals. After the tests, candidate testing module 212 updates the fitness estimate associated with each of the individuals tested.

In an embodiment, a minimum fitness level may be required for an individual to participate in competition. Individuals may be discarded from the pool based on the fitness estimate assigned to an individual based on the results of the most recent battery of tests.

The competition module 214 places individuals in the candidate pool in rank order according to their fitness estimate. A number of individuals at the top of the ranking are selected to fill an elitist pool 224, and the remaining individuals at the bottom of the ranking that do not fit in the elitist pool 224 may be discarded. During competition, a requirements checkpoint may be performed to ensure that all individuals admitted into the elitist pool 224 meet minimum requirements.

A procreation module 216 evolves a subset of individuals from the elitist pool. The subset of individuals chosen for evolution may be selected randomly. Any conventional or future-developed technique can be used for procreation. In an embodiment, conditions, outputs, or rules from parent individuals are combined in various ways to form child individuals, and then, occasionally, they are mutated. The combination process for example may include crossover— i.e., exchanging conditions, outputs, or entire rules between parent individuals to form child individuals. New individuals created through procreation begin no experience/maturity and with a fitness estimate that is undefined. These individuals are placed in candidate pool 116. Preferably, after new individuals are created by combination and/or mutation, the parent individuals and others in the elitist pool are retained in the candidate pool for the next generation of testing. In another embodiment, the parent individuals are discarded and the other elitists are retained.

After procreation, candidate testing module 212 operates again on the updated candidate pool 116, and the process repeats.

Harvesting module 218 retrieves individuals from the elitist pool. The individuals selected by the harvesting module 218 are moved from the elitist pool 224 to another EE/EC 230 for further testing or moved to the production individual population database 122 for use by production system 112 as previously described.

Figure 3:
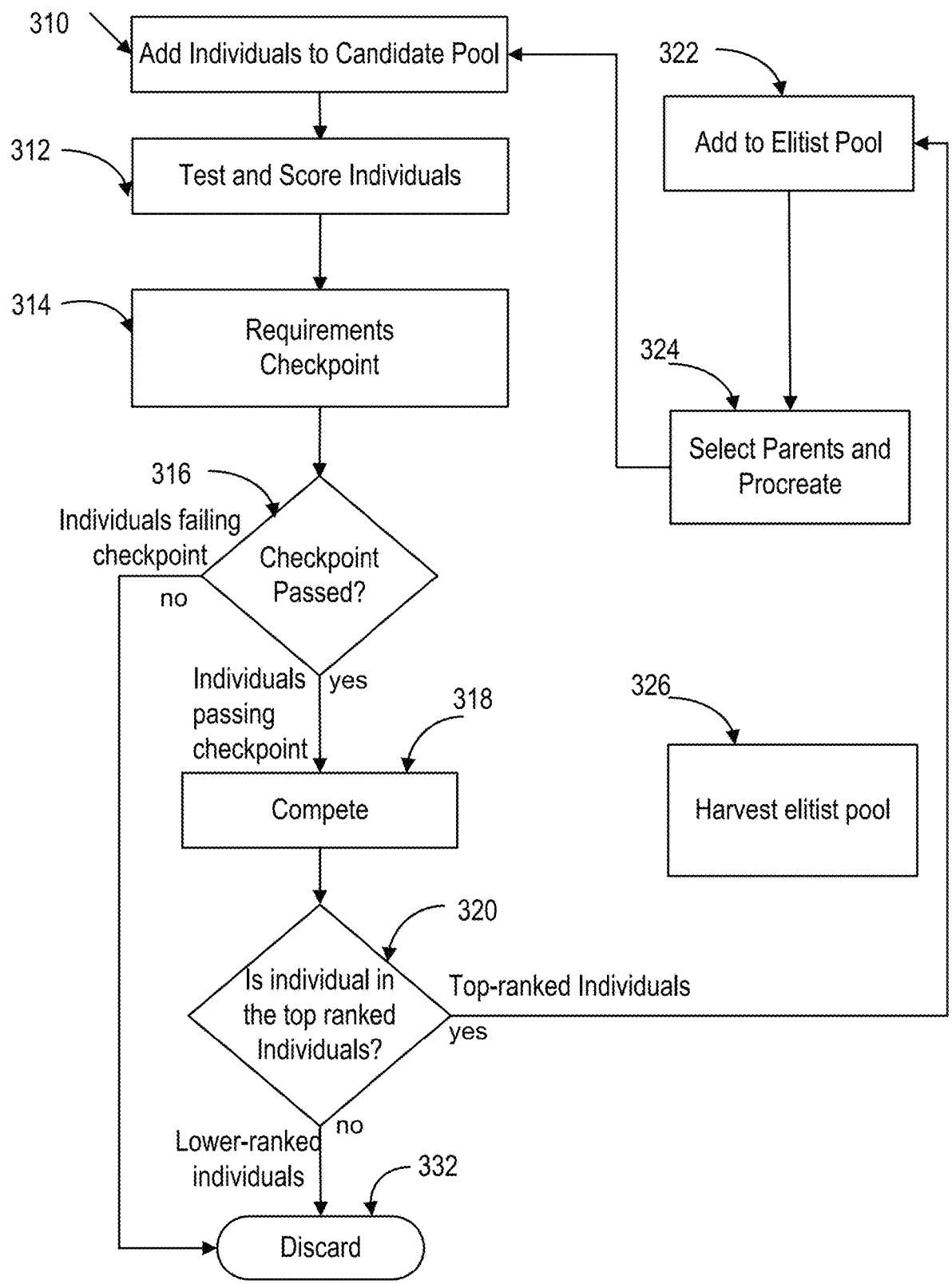
FIG. 3 is a flow diagram that illustrates a method of operation of the competition module, according to an embodiment of the invention.

FIG. 3 is a flow diagram that illustrates a method of operation of the candidate processing module 220, according to an embodiment of the invention. In Step 310, new individuals are added to the candidate pool. The added individuals may have been added from an external server or EC delegating work to the system of FIG. 2, or may be newly created individuals that are created at the very start of the operation, or may be newly created through procreation of mature and fit parent individuals. In Step 312, individuals in the candidate pool are tested and assigned a fitness estimate. In Step 314, each individual in the candidate pool undergoes a requirements checkpoint during which characteristics of the individuals are compared to a threshold representing minimum requirements. In Step 316, those individuals who do not pass the checkpoint, that is, those individuals whose characteristics do not meet or exceed the threshold, are removed from the candidate pool and selected for discarding in 332. Individuals that pass the checkpoint compete with each other to survive this generation in Step 318. Competition involves comparing the fitness estimates assigned to the candidate individuals and deciding which candidates to allow to continue training and which to select for discarding. For example, the individuals' fitness estimates may be compared to other individuals that have passed through the checkpoint, to generate a rank ordering based on the fitness estimates.

In Step 320, the top ranked individuals are selected for inclusion in the elitist pool. The elitist pool may hold n individuals which may be fewer individuals than the capacity of the candidate pool. Thus, some individuals in the candidate pool will be selected for inclusion in the elitist pool and the others will be selected for discarding. The top n-ranked individuals will be added to the elitist pool in 322, and the individuals in the candidate pool that are ranked lower than the top n-ranked individuals are discarded in 332. In other embodiments, other criteria, either additional to or instead of fitness, may be used to select individuals into the elitist pool.

In Step 324, some number of individuals is selected from the elitist pool to procreate new individuals. The parents may be selected in any way, such as randomly, based on the fitness estimate, diversity, or based on the novelty of the elitists' behavior. The genetic material of the selected progenitors (parents) is used to create new individuals that are added to the candidate pool for the next generation.

At various intervals, or at a predetermined time, in Step 326, candidate individuals in elitist pool may be reported to an up-chain server or evolutionary coordinator. In addition, individuals in the elitist pool may be harvested. Harvesting in the context of this specification means that an individual is transmitted to an evolutionary coordinator for management or further evolution or competition, or is harvested to move to the production system. Harvested individuals may be removed from the elitist pool in some embodiments, though they are not required to be removed in all embodiments.

Members of the elitist pool that are not removed from the system are placed back into the candidate pool with newly added individuals, tested, and assigned a new fitness estimate.

In the flow illustrated in FIG. 3, the requirements checkpoint is inserted between testing and competition. The flow diagram of FIG. 3 illustrates an embodiment in which the checkpoint is applied to an individual before the individual is ranked against other individuals; weeding out individuals that fail the checkpoint first reduces the effort needed to perform the rank ordering. In another embodiment, individuals compete (are ranked) first, then pass through a requirements checkpoint before being added to the elitist pool. Only applying the requirements checkpoint to the top-ranked individuals that fit in the elitist pool reduces the effort for applying the checkpoint to the smaller number of individuals that fit into the elitist pool.

In yet another embodiment, the requirements checkpoint and the competition occur in an interleaved, pipelined, or parallel fashion. For example, the individuals may be considered sequentially. Each individual first passes through the checkpoint, being checked against the requirements, and discarded if the individual fails to meet the requirements. Only if it passes does it compete with other individuals. And then, only if the individual competes successfully is it retained; otherwise the individual is discarded. Then the system checks the next individual against the checkpoint. Considering individuals sequentially avoids having to retrieve an individual twice.

In an alternate embodiment, only individuals newly added to the candidate pool on this evolutionary engine need pass through the requirements checkpoint. The testing and fitness assessment process does not change the genetic makeup of the individuals, and thus, an individual that previously passed through the requirements checkpoint need not pass through the checkpoint again, unless the embodiment is such that the requirements can change over time.

Figure 4:
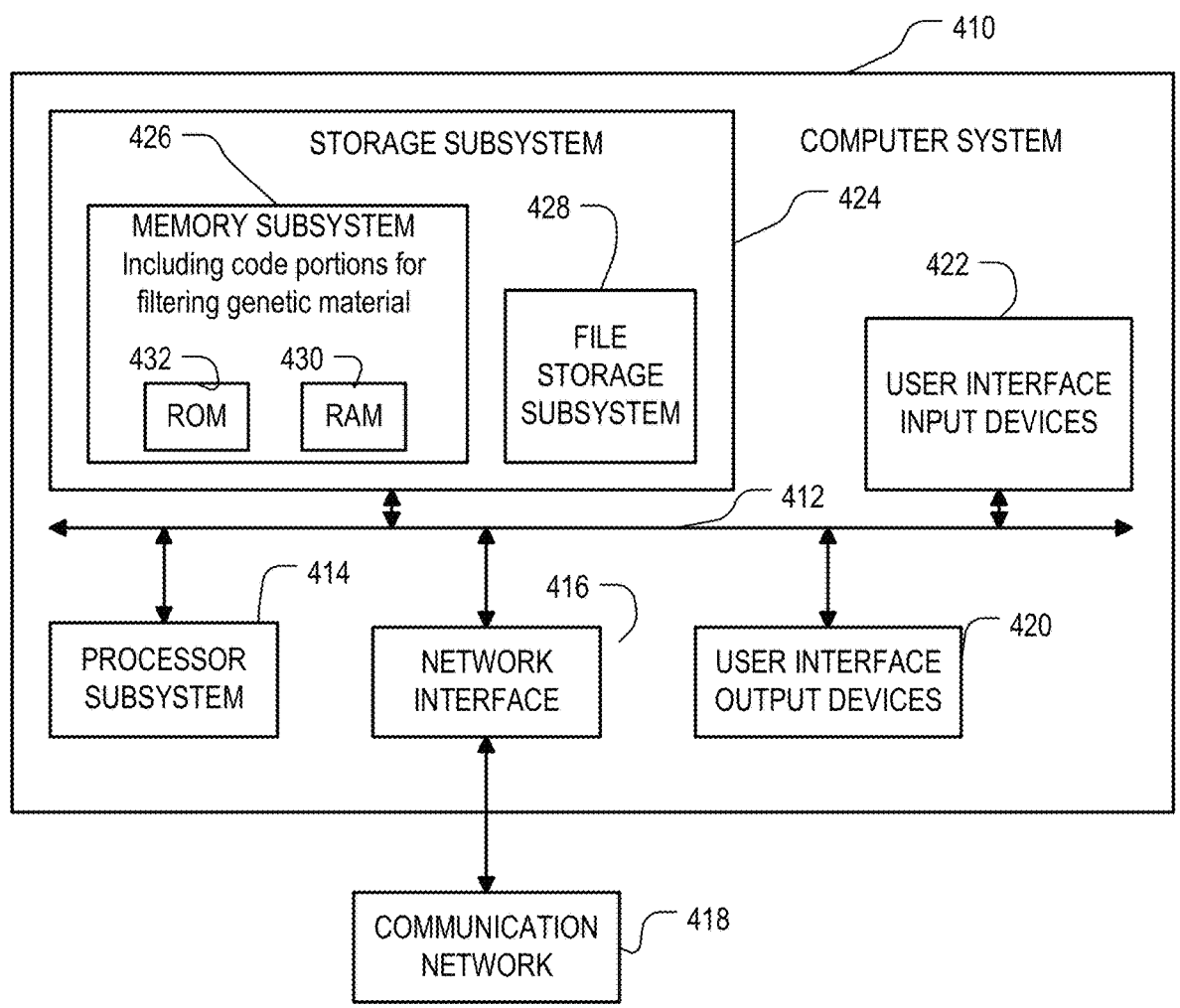
FIG. 4 is a simplified block diagram of a computer system that can be used to implement either or both of the training system or production system in FIG. 1, according to an embodiment of the invention.

FIG. 4 is a simplified block diagram of a computer system 410 that can be used to implement training system 110, production system 112, or both. While FIGS. 1 and 2 indicate individual components for carrying out specified operations, it will be appreciated that each component actually causes a computer system such as 410 to operate in the specified manner.

Computer system 410 typically includes a processor subsystem 414 which communicates with a number of peripheral devices via bus subsystem 412. These peripheral devices may include a storage subsystem 424, comprising a memory subsystem 426 and a file storage subsystem 428, user interface input devices 422, user interface output devices 420, and a network interface subsystem 416. The input and output devices allow user interaction with computer system 410. Network interface subsystem 416 provides an interface to outside networks, including an interface to communication network 418, and is coupled via communication network 418 to corresponding interface devices in other computer systems. Communication network 418 may comprise many interconnected computer systems and communication links. These communication links may be wireline links, optical links, wireless links, or any other mechanisms for communication of information. While in one embodiment, communication network 418 is the Internet, in other embodiments, communication network 418 may be any suitable computer network.

The physical hardware component of network interfaces are sometimes referred to as network interface cards (NICs), although they need not be in the form of cards: for instance they could be in the form of integrated circuits (ICs) and connectors fitted directly onto a motherboard, or in the form of macrocells fabricated on a single integrated circuit chip with other components of the computer system.

User interface input devices 422 may include a keyboard, pointing devices such as a mouse, trackball, touchpad, or graphics tablet, a scanner, a touch screen incorporated into the display, audio input devices such as voice recognition systems, microphones, and other types of input devices. In general, use of the term "input device" is intended to include all possible types of devices and ways to input information into computer system 410 or onto computer network 418.

User interface output devices 420 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 410 to the user or to another machine or computer system. In particular, an output device of the computer system 410 on which production system 112 is implemented, may include a visual output informing a user of action recommendations made by the system, or may include a communication device for communicating action signals directly to the controlled system 128. Additionally or alternatively, the communication network 418 may communicate action signals to the controlled system 128. In the financial asset trading environment, for example, the communication network 418 transmits trading signals to a computer system in a brokerage house which attempts to execute the indicated trades.

Storage subsystem 424 stores the basic programming and data constructs that provide the functionality of certain embodiments of the present invention. For example, the various modules implementing the functionality of certain embodiments of the invention may be stored in storage subsystem 424. These software modules are generally executed by processor subsystem 414. Storage subsystem 424 also stores the candidate pool 116, the training database 114, and/or the production individual population 122. Alternatively, one or more of such databases can be physically located elsewhere, and made accessible to the computer system 410 via the communication network 418.

Memory subsystem 426 typically includes a number of memories including a main random access memory (RAM) 430 for storage of instructions and data during program execution and a read only memory (ROM) 432 in which fixed instructions are stored. File storage subsystem 428 provides persistent storage for program and data files, and may include a hard disk drive, a floppy disk drive along with associated removable media, a CD ROM drive, an optical drive, or removable media cartridges. The databases and modules implementing the functionality of certain embodiments of the invention may have been provided on a computer readable medium such as one or more CD-ROMs, and may be stored by file storage subsystem 428. The host memory 426 contains, among other things, computer instructions which, when executed by the processor subsystem 414, cause the computer system to operate or perform functions as described herein. As used herein, processes and software that are said to run in or on "the host" or "the computer", execute on the processor subsystem 414 in response to computer instructions and data in the host memory subsystem 426 including any other local or remote storage for such instructions and data.

Bus subsystem 412 provides a mechanism for letting the various components and subsystems of computer system 410 communicate with each other as intended. Although bus subsystem 412 is shown schematically as a single bus, alternative embodiments of the bus subsystem may use multiple busses.

Computer system 410 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 410 depicted in FIG. 4 is intended only as a specific example for purposes of illustrating the preferred embodiments of the present invention. Many other configurations of computer system 410 are possible having more or less components than the computer system depicted in FIG. 4.

As used herein, a given event is "responsive" to a predecessor event if the predecessor event influenced the given event. If there is an intervening processing element, step or time period, the given event can still be "responsive" to the predecessor event. If the intervening processing element or step combines more than one event, the signal output of the processing element or step is considered "responsive" to each of the event inputs. If the given event is the same as the predecessor event, this is merely a degenerate case in which the given event is still considered to be "responsive" to the predecessor event. "Dependency" of a given event upon another event is defined similarly.

As used herein, the "identification" of an item of information does not necessarily require the direct specification of that item of information. Information can be "identified" by simply referring to the actual information through one or more layers of indirection, or by identifying one or more items of different information which are together sufficient to determine the actual item of information.

Applicants hereby disclose in isolation each individual feature described herein and each combination of two or more such features, to the extent that such features or combinations are capable of being carried out based on the present specification as a whole in light of the common general knowledge of a person skilled in the art, irrespective of whether such features or combinations of features solve any problems disclosed herein, and without limitation to the scope of the claims. Applicants indicate that aspects of the present invention may consist of any such feature or combination of features. In view of the foregoing description it will be evident to a person skilled in the art that various modifications may be made within the scope of the invention.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. In particular, and without limitation, any and all variations described, suggested or incorporated by reference in the Background section of this patent application are specifically incorporated by reference into the description herein of embodiments of the invention. In addition, any and all variations described, suggested or incorporated by reference herein with respect to any one embodiment are also to be considered taught with respect to all other embodiments. The embodiments described herein were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

The invention claimed is:

1. A computer-implemented data mining system for evolving a solution to a predetermined problem in a predetermined domain, for use with a data mining training database containing training data, comprising:

a memory storing a database having a candidate pool comprising a set of candidate solution individuals, each candidate solution individual identifying a rule set including a plurality of conditions and at least one corresponding consequence to be asserted in dependence upon the conditions, each candidate solution individual further having associated therewith a respective testing experience level and a respective fitness estimate; and a candidate evolution module which:
- in a candidate testing step, tests solution individuals from the candidate pool on the training data, each solution individual being tested undergoing a respective battery of at least one trial on the training data and thereby increasing the solution individual's testing experience level, each trial applying the rule set of the respective solution individual to the training data to propose an output,
- in a fitness update step, updates the fitness estimate associated with each of the solution individuals being tested in dependence upon both the training data and the outputs proposed by the respective solution individual in the battery of trials,
- in a requirements checking step, selects solution individuals for discarding from the candidate pool which do not meet a predetermined minimum behavioral requirement for operating in production, wherein a behavioral requirement is a measure of the select solution individual's activity in applying the select solution individual's rule set to the training data to produce an output,
- in a competition step, selects solution individuals for discarding from the candidate pool in dependence upon their updated fitness estimates,
- in a procreation step, forms new solution individuals in dependence upon a respective set of at least one parent individual from the candidate pool, and
- in a deployment step, provides for deployment of selected ones of the solution individuals from the candidate pool in the predetermined domain against problem data to generate a solution to the predetermined problem.

2. The system of claim 1, wherein the requirements checking step considers for discarding only solution individuals whose testing experience level is at least as high as a predetermined minimum experience level.

3. The system of claim 2, wherein the predetermined minimum experience level is equal to a maturity level which is a testing experience level at which the competition step initially considers solution individuals for discarding.

4. The system of claim 1, wherein the predetermined minimum behavioral requirement is a threshold activity level of the solution individual.

5. The system of claim 1, wherein the predetermined minimum behavioral requirement is a threshold activity level of a subject rule in the solution individual.

6. The system of claim 1, wherein the predetermined minimum behavioral requirement is a threshold portion of trials on which the solution individual has been tested and which caused a change in a stateful object associated with the solution individual.

7. The system of claim 1, wherein the candidate evolution module further includes a second requirements checking step, in which solution individuals are selected for discarding from the candidate pool which do not meet a second predetermined minimum behavioral requirement for operating in production.

8. The system of claim 1, wherein the candidate evolution module further includes a step of performing the candidate testing step, the fitness update step, the requirements checking step, the competition step, and the procreation step, for a plurality of iterations, and wherein the requirements checking step occurs after each occurrence of the candidate testing step and before the first subsequent occurrence of the procreation step, in each iteration of the plurality of iterations.

9. The system of claim 1, wherein the candidate evolution module further includes a step of performing the candidate testing step, the fitness update step, the requirements checking step, the competition step, and the procreation step, for a plurality of iterations, and wherein the requirements checking step occurs after each occurrence of the candidate testing step and before the first subsequent occurrence of the competition step, in each iteration of the plurality of iterations.

10. The system of claim 1, wherein the candidate evolution module further includes a step of performing the candidate testing step, the fitness update step, the requirements checking step, the competition step, and the procreation step, for a plurality of iterations, and wherein the requirements checking step occurs after each occurrence of the competition step and before the first subsequent occurrence of the procreation step, in each iteration of the plurality of iterations.

11. The system of claim 1, wherein in response to selection of a particular solution individual for discarding, the particular solution individual is precluded from participating fully in any subsequent occurrence of the procreation step.

12. The system of claim 11, wherein in response to selection of the particular solution individual for discarding, the particular solution individual is precluded from participating in any subsequent occurrence of the procreation step.

13. A computer-implemented data mining process for evolving a solution to a predetermined problem in a predetermined domain, for use with a data mining training database containing training data, comprising:

storing in a database a set of candidate solution individuals as a candidate pool, each candidate solution individual identifying a rule set including a plurality of conditions and at least one corresponding consequence to be asserted in dependence upon the conditions, each candidate solution individual further having associated therewith a respective testing experience level and a respective fitness estimate;

evolving by a processor, candidate solution individuals in accordance with the following steps:

testing solution individuals from the candidate pool on the training data, each solution individual being tested undergoing a respective battery of at least one trial on the training data and thereby increasing the solution individual's testing experience level, each trial applying the rule set of the respective solution individual to the training data to propose an output, updating the fitness estimate associated with each of the solution individuals being tested in dependence upon both the training data and the outputs proposed by the respective solution individual in the battery of trials, selecting by a requirements checking module solution individuals for discarding from the candidate pool which do not meet a first predetermined minimum behavioral requirement for operating in production, wherein a behavioral requirement is a measure of the select solution individual's activity in applying the select solution individual's rule set to the training data to produce an output, selecting by a competition module solution individuals for discarding from the candidate pool in dependence upon their updated fitness estimates, forming by a procreation module new solution individuals in dependence upon a respective set of at least one parent individual from the candidate pool, and deploying selected ones of the solution individuals from the candidate pool in the predetermined domain against problem data to generate a solution to the predetermined problem.

14. The process of claim 13, further including selecting by the requirements checking module solution individuals for discarding from the candidate pool only solution individuals whose testing experience level is at least as high as a predetermined minimum experience level.

15. The process of claim 14, wherein the predetermined minimum experience level is equal to a maturity level which is a testing experience level at which the requirements checking module initially considers solution individuals for discarding.

16. The process of claim 13, wherein the first predetermined minimum behavioral requirement is a threshold activity level of the solution individual.

17. The process of claim 13, wherein the first predetermined minimum behavioral requirement is a threshold activity level of a subject rule in the solution individual.

18. The process of claim 13, wherein the first predetermined minimum behavioral requirement is a threshold portion of trials on which the solution individual has been tested and which caused a change in a stateful object associated with the solution individual.

19. The process of claim 13, further comprising selecting by the requirements checking module, solution individuals for discarding from the candidate pool which do not meet a second predetermined minimum behavioral requirement for operating in production.

20. The process of claim 13, wherein the steps of testing the solution individuals, updating the fitness estimate, selecting by a requirements checking module, selecting by a competition module, and forming by a procreation module, are repeated for a plurality of iterations, and wherein the selecting by a requirements checking module occurs after each occurrence of the testing of the solution individuals and before a first subsequent occurrence of the forming by a procreation module, in each iteration of the plurality of iterations.

21. The process of claim 13, wherein the steps of testing the solution individuals, updating the fitness estimate, selecting by a requirements checking module, selecting by a competition module, and forming by a procreation module, are repeated for a plurality of iterations, and wherein the selecting by a requirements checking module occurs after each occurrence of the testing of the solution individuals and before a first subsequent occurrence of the selecting by a competition module, in each iteration of the plurality of iterations.

22. The process of claim 13, wherein the steps of testing the solution individuals, updating the fitness estimate, selecting by a requirements checking module, selecting by a competition module, and forming by a procreation module, are repeated for a plurality of iterations, and wherein the selecting by a requirements checking module occurs after each occurrence of the selecting by a competition module and before a first subsequent occurrence of the forming by a procreation module, in each iteration of the plurality of iterations.

23. The system of claim 13, wherein in response to selection of a particular solution individual for discarding, the particular solution individual is precluded from participating fully in any subsequent occurrence of the forming by a procreation module.

24. The system of claim 23, wherein in response to selection of the particular solution individual for discarding, the particular solution individual is precluded from participating in any subsequent occurrence of the procreation step.

* * * * *